United States Patent
Cohn et al.

(10) Patent No.: US 11,723,708 B2
(45) Date of Patent: Aug. 15, 2023

(54) METHOD FOR REMOVING A TISSUE LESION

(71) Applicant: Prana Thoracic, Inc., Houston, TX (US)

(72) Inventors: William Cohn, Bellaire, TX (US); Terry Daglow, Houston, TX (US); Steven Nguyen, Cypress, TX (US); Matthew Kuhn, Houston, TX (US); Fergus Wong, Houston, TX (US); Colin Brahmstedt, Houston, TX (US)

(73) Assignee: Prana Thoracic, Inc., Houston, TX (US)

( * ) Notice: Subject to any disclaimer, the term of this patent is extended or adjusted under 35 U.S.C. 154(b) by 972 days.

(21) Appl. No.: 16/512,628

(22) Filed: Jul. 16, 2019

(65) Prior Publication Data

US 2020/0038090 A1     Feb. 6, 2020

Related U.S. Application Data

(60) Provisional application No. 62/756,234, filed on Nov. 6, 2018, provisional application No. 62/749,302, filed
(Continued)

(51) Int. Cl.
    *A61B 18/08*                 (2006.01)
    *A61B 17/34*                 (2006.01)
    (Continued)

(52) U.S. Cl.
    CPC ........ *A61B 18/082* (2013.01); *A61B 10/0266* (2013.01); *A61B 10/04* (2013.01); *A61B 17/3403* (2013.01); *A61B 17/3423* (2013.01); *A61B 18/1206* (2013.01); *A61B 2010/045* (2013.01); *A61B 2018/00541* (2013.01);
(Continued)

(58) Field of Classification Search
    CPC .............. A61B 18/082; A61B 18/1206; A61B 10/0266; A61B 10/04; A61B 17/3403; A61B 17/3423; A61B 2010/045; A61B 2018/00541; A61B 2018/00577;
(Continued)

(56) References Cited

U.S. PATENT DOCUMENTS 4,735,194 A * 4/1988 Stiegmann ............. A61B 1/015
                                                                                 600/117
5,651,788 A * 7/1997 Fleischer ............... A61B 18/14
                                                                                 606/46

(Continued)

FOREIGN PATENT DOCUMENTS

| DE | 102016101915 A1 | 8/2017 |
| EP | 1340469 A1 | 9/2003 |
| WO | WO2011094110 A1 | 8/2011 |

OTHER PUBLICATIONS

European Search Report for corresponding EPA No. 19189128.2 dated Oct. 9, 2019.
(Continued)

*Primary Examiner* — Christopher A Flory

(57) ABSTRACT

A method for removing a tissue lesion where an anchor is established with the lesion. A channel is created in the tissue leading to the anchored lesion. A tissue core is created which includes the lesion. The tissue core is ligated, amputated and removed from the channel.

11 Claims, 5 Drawing Sheets

Related U.S. Application Data on Oct. 23, 2018, provisional application No. 62/744,797, filed on Oct. 12, 2018, provisional application No. 62/728,170, filed on Sep. 7, 2018, provisional application No. 62/712,545, filed on Jul. 31, 2018.

(51) Int. Cl.
*A61B 18/12* (2006.01)
*A61B 10/04* (2006.01)
*A61B 10/02* (2006.01)
*A61B 18/00* (2006.01)

(52) U.S. Cl.
CPC .............. *A61B 2018/00577* (2013.01); *A61B 2018/00595* (2013.01); *A61B 2018/00601* (2013.01); *A61B 2018/126* (2013.01)

(58) Field of Classification Search
CPC ........... A61B 2018/00595; A61B 2018/00601; A61B 2018/126
See application file for complete search history.

(56) References Cited

U.S. PATENT DOCUMENTS

| | | | |
|---|---|---|---|
| 5,843,108 | A | 12/1998 | Samuels |
| 6,022,362 | A * | 2/2000 | Lee ................... A61B 10/0266 600/564 |
| 6,974,467 | B1 | 12/2005 | Gonzales, Jr. |
| 2002/0059938 | A1* | 5/2002 | Fogarty ................. A61B 90/39 128/899 |
| 2004/0147917 | A1 | 7/2004 | Mueller |
| 2007/0156156 | A1* | 7/2007 | Badie ................ A61B 17/3421 606/129 |
| 2010/0174306 | A1 | 7/2010 | Mitelberg |
| 2011/0105841 | A1* | 5/2011 | Kutikov ............... A61B 5/6839 600/104 |
| 2014/0277039 | A1 | 9/2014 | Liberatore |
| 2018/0140319 | A1 | 5/2018 | Saidi |

OTHER PUBLICATIONS

European Search Report for corresponding EPA No. 19189139.9 dated Oct. 9, 2019.

* cited by examiner

METHOD FOR REMOVING A TISSUE LESION

CROSS-REFERENCES TO OTHER RELATED PATENT APPLICATIONS

This application claims priority from application Ser. No. 62/712,545 filed Jul. 31, 2018, which is incorporated herein by reference in its entirety.

This application claims priority from application Ser. No. 62/728,170 filed Sep. 7, 2018, which is incorporated herein by reference in its entirety.

This application claims priority from application Ser. No. 62/744,797 filed Oct. 12, 2018, which is incorporated herein by reference in its entirety.

This application claims priority from application Ser. No. 62/749,302 filed Oct. 23, 2018, which is incorporated herein by reference in its entirety.

This application claims priority from application Ser. No. 62/756,234 filed Nov. 6, 2018, which is incorporated herein by reference in its entirety.

BACKGROUND OF THE INVENTION

1. Field of the Invention

The present invention relates to a system, device and method for tissue resection. More particularly, the present invention relates to a system, device and method for lesion removal.

2. Discussion of the Related Art

Cancer is not a single disease, but rather a collection of related diseases that can start essentially anywhere in the body. Common amongst all types of cancer is that the body's cells begin to divide without stopping, proliferating and potentially spreading into surrounding tissues. In the normal course of events, cells grow and divide to form new cells as required by the body and when they become damaged or old, they die, and new cells replace the damaged or old cells; however, cancer interrupts this process. With cancer, the cells become abnormal, and cells that should die do not and new cells form when they are not needed. These new cells can reproduce or proliferate without stopping and may form growths called tumors.

Cancerous tumors are malignant, which means they can spread into or invade surrounding healthy tissue. In addition, cancer cells can break off and travel to remote areas in the body through blood or in the lymph system. Benign tumors, unlike malignant tumors, do not spread or invade surrounding tissue; however, they may grow large and cause damage. Both malignant and benign tumors may be removed or treated. Malignant tumors tend to grow back whereas benign tumors can grow back but are much less likely to do so.

Cancer is a genetic disease in that it is caused by changes in the genes that control the ways that cells function, especially in how they grow and divide. Genetic changes that cause cancer may be inherited or they may arise over an individual's lifetime as a result of errors that occur as cells divide or because of damage to DNA caused by certain environmental exposure, for example, industrial/commercial chemicals and ultraviolet light. The genetic changes that may cause cancer tend to affect three types of genes; namely proto-oncogenes which are involved in normal cell growth and division, tumor suppressor genes which are also involved in controlling cell growth and division, and DNA repair genes which, as the name implies, are involved in repairing damaged DNA.

More than one-hundred distinct types of cancer have been identified. The type of cancer may be named for the organ or tissue where the cancers arise, for example, lung cancer, or the type of cell that formed them, for example squamous cell cancer. Cancer, unfortunately, is a leading cause of death both in the United States and world-wide. According to the World Health Organization, the number of new cancer cases will rise to twenty-five (25) million per year over the next two decades.

Lung cancer is one of the most common cancers today. According to the World Cancer Report 2014 from the World Health Organization, lung cancer occurred in 14 million people and resulted in 8.8 million deaths world-wide, making it the most common cause of cancer-related death in men and the second most common cause of cancer-related death in women. Lung cancer or lung carcinoma is a malignant lung tumor that if left untreated can metastasize into neighboring tissues and organs. The majority of lung cancer is caused by long-term tobacco smoking; however, about 10 to 15 percent of lung cancer cases are not tobacco related. These non-tobacco cases are most often caused by a combination of genetic factors and exposure to certain environmental conditions, including radon gas, asbestos, secondhand tobacco smoke, other forms of air pollution, and other agents. The chance of surviving lung cancer as well as other forms of cancer depends on early detection and treatment.

When a lesion is detected in the lungs, a biopsy is performed and sent for study. If it is determined that the lesion is cancerous, a second procedure may be performed to remove the cancer. If the biopsy reveals no cancer, it may be correct, or the biopsy did not pick the cancerous cells. Accordingly, there exists a need for removing the whole lesion in one single procedure so that an accurate diagnosis may be performed.

SUMMARY OF THE INVENTION

The system, device and method for performing lung lesion removal of the present invention overcomes the limitations associated with the prior art.

The present invention relates to a system, device and method for performing lung lesion removal. A lung needle biopsy is typically performed when an abnormality is found on an imaging test, for example, an X-ray or CAT scan. In a lung needle biopsy, a fine needle is used to remove sample of lung tissue for examining under a microscope to determine the presence of abnormal cells. Tissue diagnosis is challenging in small (<6 mm) and intermediate (6-12 mm) nodules. CT guided biopsy of peripheral lesions, either through the chest wall (80%) or by means of a bronchoscope (20%) yields only a 0.001-0.002 cm2 of diagnostic tissue, and as such, cancer, when present, is only successfully identified in 60% of small and intermediate nodules. Although bronchoscopic techniques and technology continue to evolve, biopsy accuracy, specificity, and sensitivity will always be limited when dealing with small and intermediate nodules in the periphery of the lung.

If it is determined that the lesion is cancerous, a second procedure may be performed to remove the lesion and then followed up with chemotherapy and/or radiation. The second procedure most likely involves lung surgery. These procedures are typically done through an incision between the ribs. There are a number of possible procedures depending on the state of the cancer. Video-assisted thoracic surgery is a less invasive procedure for certain types of lung cancer. It is performed through small incisions utilizing an endoscopic approach and is typically utilized for performing wedge resections of smaller lesions close to the surface of a lung. In a wedge resection, a portion of the lobe is removed. In a sleeve resection, a portion of a large airway is removed thereby preserving more lung function.

Nodules deeper than 2-3 cm from the lung surface, once identified as suspicious for cancer, are difficult to localize and excise using laparoscopic or robotic lung sparing technique despite pre-procedure image guided biopsy and localization. Thus, surgeons perform an open thoracotomy or lobectomy to remove lung nodules that are 2-3 cm from the lung surface. A thoracotomy is an open approach surgery in which a portion of a lobe, a full lobe or an entire lung is removed. In a pneumonectomy, an entire lung is removed. This type of surgery is obviously the most aggressive. In a lobectomy, an entire section or lobe of a lung is removed and represents a less aggressive approach than removing the entire lung. All thoracoscopic lung surgeries require trained and experienced thoracic surgeons and the favorability of surgical outcomes track with operative experience.

Any of these types of lung surgery is a major operation with possible complications which depend on the extent of the surgery as well as the patient's overall health. In addition to the reduction in lung function associated with any of these procedures, the recovery may take from weeks to months. With a thoracotomy, spreading of the ribs is required, thereby increasing postoperative pain. Although video-assisted thoracic surgery is less invasive, there can still be a substantial recovery period. In addition, once the surgery is complete, full treatment may require a system chemotherapy and/or radiation treatment.

As set forth above, a fine needle biopsy may not prove to be totally diagnostic. The fine needle biopsy procedure involves guiding a needle in three-dimensional space under two-dimensional imaging. Accordingly, the doctor may miss the lesion, or even if he or she hits the correct target, the section of the lesion that is removed through the needle may not contain the cancerous cells or the cells necessary to assess the aggressiveness of the tumor. A needle biopsy removes enough tissue to create a smear on a slide. The device of the present invention is designed to remove the entire lesion, or a substantial portion of it, while minimizing the amount of healthy lung tissue removal. This offers a number of advantages. Firstly, the entire lesion may be examined for a more accurate diagnosis without confounding sampling error, loss of cell packing or gross architecture. Secondly, since the entire lesion is removed, a secondary procedure as described above may not be required. Thirdly, localized chemotherapy and/or energy-based tumor extirpation, such as radiation, may be introduced via the cavity created by the lesion removal.

In at least one embodiment, the invention defines a method for removing a tissue lesion including anchoring to the tissue lesion; creating a channel in the tissue leading to the tissue lesion; creating a tissue core including the tissue lesion; ligating the tissue core at a ligation point downstream from the tissue lesion; amputating the tissue core form the tissue between the ligation point and the tissue lesion; and removing the tissue core from the channel.

In keeping with aspects of the invention, the sleeve may be inserted in the channel prior to or after removing the tissue core. The sleeve may also be anchored to the tissue. In keeping with another aspect of the invention, a localized treatment may be delivered through the sleeve.

In some embodiments, creating a tissue core includes cauterizing and cutting tissue. Ligating tissue may include tissue may include cauterizing tissue at a specific location known as the ligation point. Amputation of the tissue core may be performed with a snare, an energized wire or any other device capable of slicing tissue.

In some embodiments, the tissue core is created by first sealing blood vessels then slicing tissue to form the core.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The resection device of the present invention comprises an energy-based arrangement capable of penetrating tissue towards a target lesion. In one embodiment depicted in FIG. 1, tissue resection device 1100 includes an outer tube 1105 is provided having a distal edge profile and having an inner diameter $ID_{outer}$. A coil 1110 is attached to outer tube 1105 where the coil turns are spaced from and opposed to a distal end of outer tube 1105. Coil 1110 preferably has a slightly blunted tip 1115 to minimize the possibility that it will penetrate through a blood vessel while being sufficiently sharp to penetrate tissue such as pleura and parenchyma. In some embodiments, coil 1110 may take the form of a helix having a constant or variable pitch. Coil 1110 may also have a variable cross-sectional geometry. An electrode 1130 is disposed on a surface or embedded within coil 1110.

Figure 1:
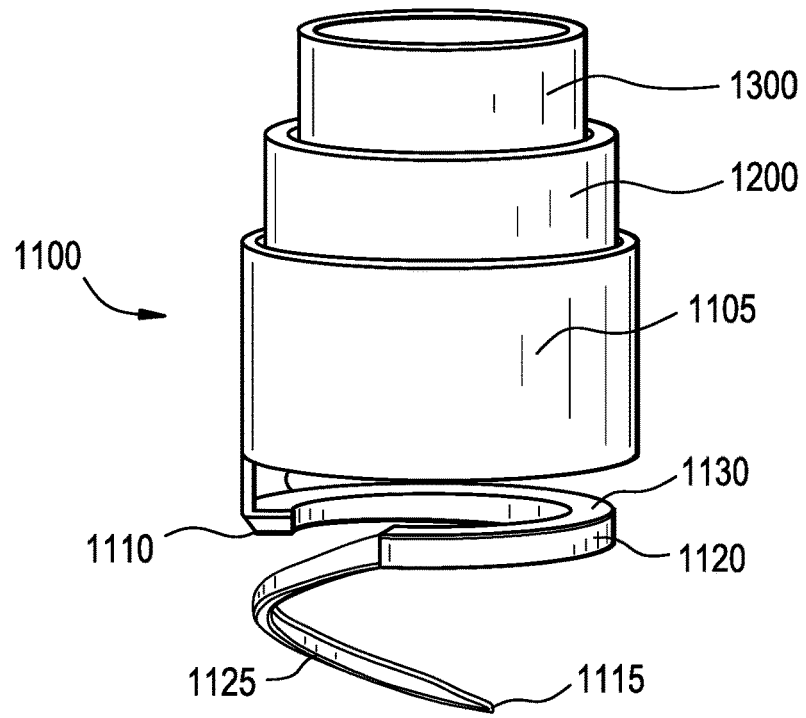
FIG. 1 depicts a tissue resection device in accordance with an embodiment of the invention.

In some embodiments, as illustrated in FIG. 1, coil 1110 may include a plurality of contiguous coil segments, e.g., coil segments 1120 and 1125. Coil segment 1120 comprises a helical member having a pitch of zero, e.g., a generally planar open ring structure, having an inner diameter $ID_{coil}$ and an outer diameter $OD_{coil}$. Coil segment 1125 comprises a helical structure of constant or variable pitch and constant or variable cross-sectional geometry. In this embodiment, electrode 1130 may be disposed on a surface of or embedded in coil segment 1120.

Figure 2:
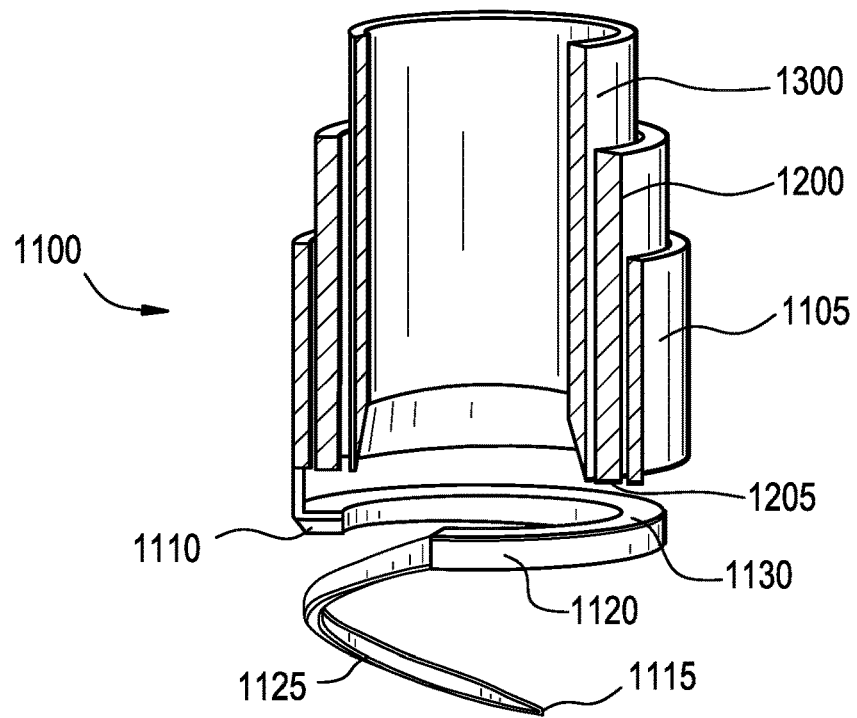
FIG. 2 illustrates a sectional view of the tissue resection device of FIG. 1.

A central tube 1200 is provided having a distal end with an edge profile comprising one or more surface segments and having an outer diameter $OD_{central}$ and an inner diameter $ID_{central}$. As illustrated in FIG. 2, an electrode 1205 is disposed on or embedded within at least one of the surface segments. Central tube 1200 is slidably disposed within outer tube 1105 and positioned such that electrode 1205 opposes and overlaps at least a portion of electrode 1130. The space between electrode 1205 and electrode 1130 is referred to as the tissue clamping zone. In keeping with an aspect of the invention, $OD_{central} > OD_{coil}$ and $OD_{coil} > ID_{central}$. In some embodiments, $OD_{central}$ is about equal to $OD_{coil}$. Accordingly, Central tube 1200 may be advanced through the tissue clamping zone towards coil 1110 such that electrode 1205 abuts electrode 1130.

A cutting tube 1300 is slidably disposed within central tube 1200. The distal end of cutting tube 1300 is provided with a knife edge to facilitate tissue cutting.

To enable tissue resection, the resection device 1100 may be inserted into tissue and outer tube 1105 may be advanced a predetermined distance towards a target. Coil segment 1125 allows the device to penetrate the tissue in a manner similar to a cork screw. As coil segment 1125 penetrates tissue, any vessel in its path is either moved to planar coil segment 1120 or pushed away from the coil 1100 for subsequent turns. Coil tip 1115 is made blunt enough to minimize chances that it will penetrate through a blood vessel while still sharp enough to penetrate certain tissue such as the lung pleura and parenchyma. Central tube 1200 may then be advanced a predetermined distance towards the target. Any vessels that are disposed in the tissue clamping zone will be clamped between electrode 1130 and electrode 1205. The vessels can then be sealed by the application of bipolar energy to electrode 1130 and electrode 1205. Once blood vessels are sealed, cutting tube 1300 is advanced to core the tissue to the depth that outer tube 1105 has reached. The sealing and cutting process can be repeated to create a core of desired size.

Figure 3:
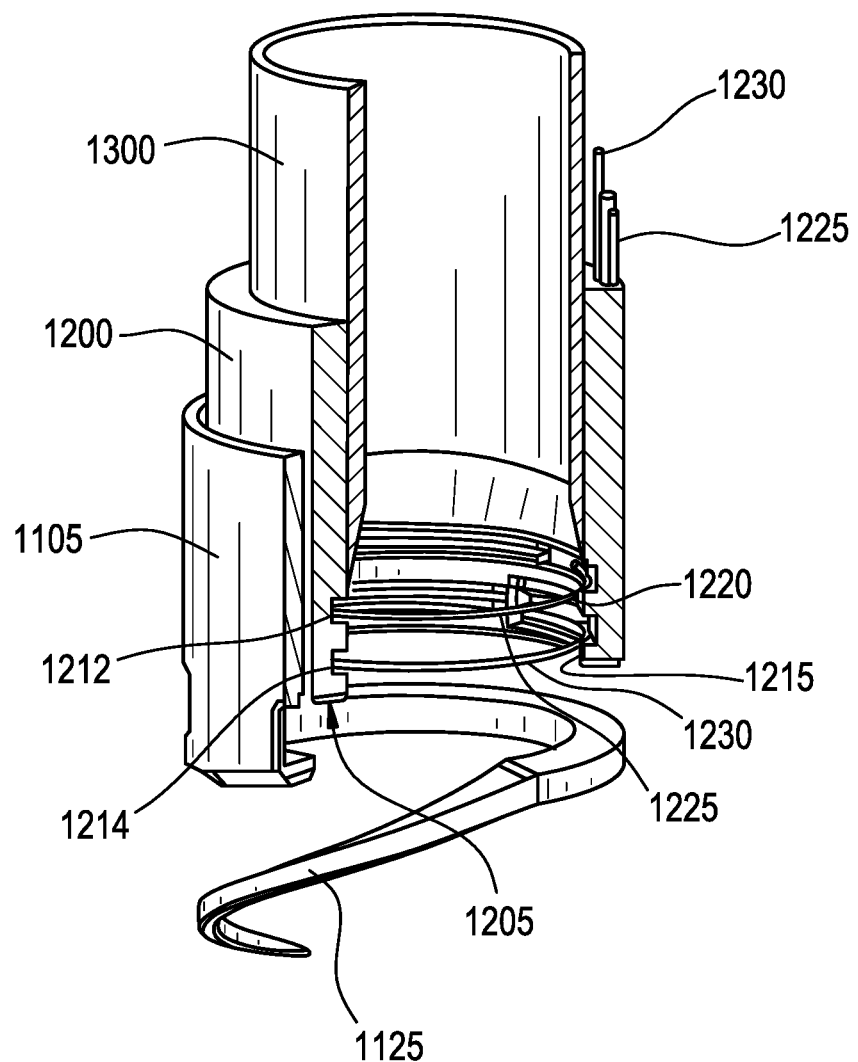
FIG. 3 shows a sectional view of a tissue resection device in accordance with an embodiment of the invention.

In keeping with an aspect of the invention, the resection device may be further configured to dissect a target lesion and seal tissue proximate the dissection point. To facilitate dissection and sealing, as illustrated in FIG. 3, central tube 1200 is provided with a ligation snare 1230, first and second ligation electrodes 1215 and 1220, an amputation snare 1225 and a ligation snare 1230. As used herein, the word "snare" refers to a flexible line, e.g., a string or a wire. The inner wall surface of central tube 1200 includes upper and lower circumferential grooved pathways 1212 and 1214 disposed proximate the distal end. The first and second ligation electrodes 1215 and 1220 are disposed on the inner wall of central tube 1200 such that lower circumferential groove 1214 is between them. Upper grooved pathway 1212 is disposed axially above ligation electrodes 1215 and 1220.

Ligation snare 1230 is disposed in lower circumferential groove 1214 and extends through central tube 1200 and axially along the outer wall surface to a snare activation mechanism (not shown). Amputation snare 1225 is disposed in upper circumferential groove 1212 and extends through central tube 1200 and axially along the outer wall surface to a snare activation mechanism (not shown). The outer surface of central tube 1200 may be provided with a plurality of axially extending grooved pathways which receive amputation snare 1225, ligation snare 1230 and are in communication with upper and lower circumferential grooved pathways 1212 and 1214. In addition, electrode leads for ligation electrodes 1215 and 1220 may extend to an energy source via the axially extending grooved pathways.

In operation, the resection device of this embodiment can detach and seal the tissue core. Cutting tube 1300 may be retracted to expose ligation snare 1230 which is preferably made of flexible line, e.g., suture. Ligation snare 1230 may be engaged to snag tissue and pull tissue against the inner wall surface between first and second ligation electrodes 1215 and 1220. Bipolar energy is then applied to first and second electrodes 1215 and 1220 to seal, i.e., cauterize, the tissue. Once sealed, cutting tube 1300 may be further retracted to expose amputation snare 1225 which may then be activated to sever the tissue core upstream from the point where the tissue was sealed (ligation point). In some embodiments, amputation snare 1225 has a smaller diameter than that of ligation snare 1230. The smaller diameter facilitates tissue slicing. Accordingly, the resection device 1100 according to this embodiment both creates a tissue core and disengages the core from surrounding tissue.

In an alternative embodiment, the resection device of the invention is provided with a single snare disposed between ligation electrodes which both ligates and cuts tissue. In this embodiment, the single snare first pulls tissue against the inner wall surface of central tube 1200 between ligation electrodes 1215 and 1220. Bipolar energy is then applied to first and second electrodes 1215 and 1220 to seal, i.e., cauterize, the tissue. Once sealed, the snare is further pulled to sever the tissue core.

Figure 4:
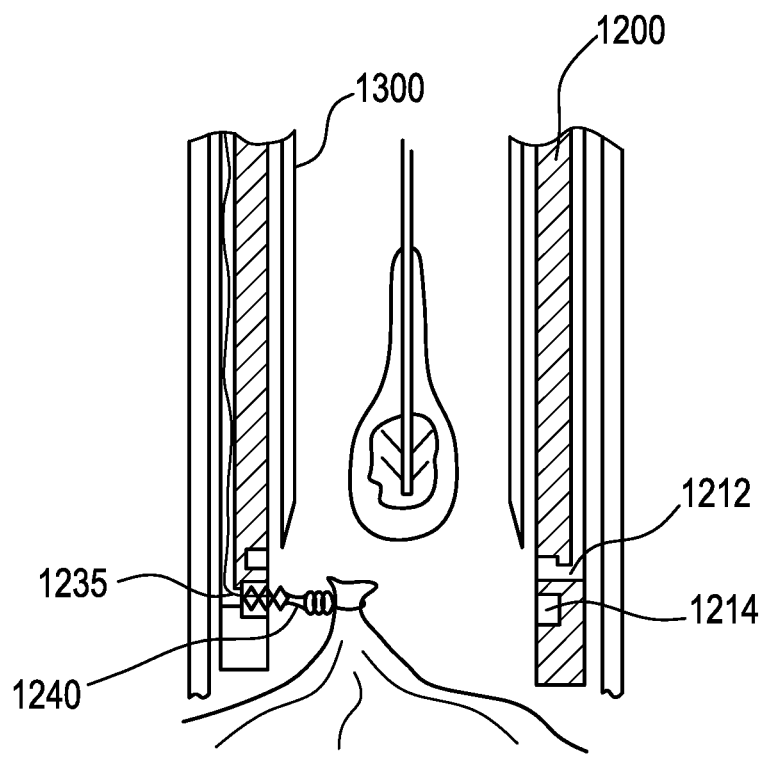
FIG. 4 depicts a sectional view of a tissue resection device in accordance with an embodiment of the invention.

In yet another embodiment, cutting and sealing may be performed without employing electrodes. In this embodiment, ligation snare 1230 includes a set of knots 1235 and 1240 which tighten under load, shown, for example, in FIG. 4. Ligation is performed by retracting cutting tube 1300 to expose ligation snare 1210 and activating ligation snare 1230 which lassos tissue as ligation knot tightens. Once the tissue is lassoed, cutting tube 1300 may be further retracted to expose amputation snare 1225 which may then be activated to sever the tissue core upstream from the point where the point where the tissue was lassoed.

The present invention also contemplates a method and system for using the resection device to remove tissue lesions, for example, lung lesions. The method generally comprises anchoring the lesion targeted for removal, creating a channel in the tissue leading to the target lesion, creating a tissue core which includes the anchored lesion, ligating the tissue core and sealing the surrounding tissue, and removing the tissue core including the target lesion from the channel.

Anchoring may be performed by, any suitable structure for securing the device to the lung. Once the lesion is anchored, a channel may be created to facilitate insertion of resection device 1100. The channel may be created by making an incision in the lung area and inserting a tissue dilator and port into the incision. A tissue core which includes the anchored lesion may be created. In keeping with the invention, resection device 1100 may be inserted into the channel and used to create the tissue core, to ligate the tissue core and to seal the tissue core and sever it from the surrounding tissue as described hereinabove. The tissue core may then be removed from the channel. In keeping with the invention, a cavity port may be inserted in the channel to facilitate subsequent treatment of the target lesion site through chemotherapy and/or energy-based tumor extirpation such as radiation.

Figure 5:
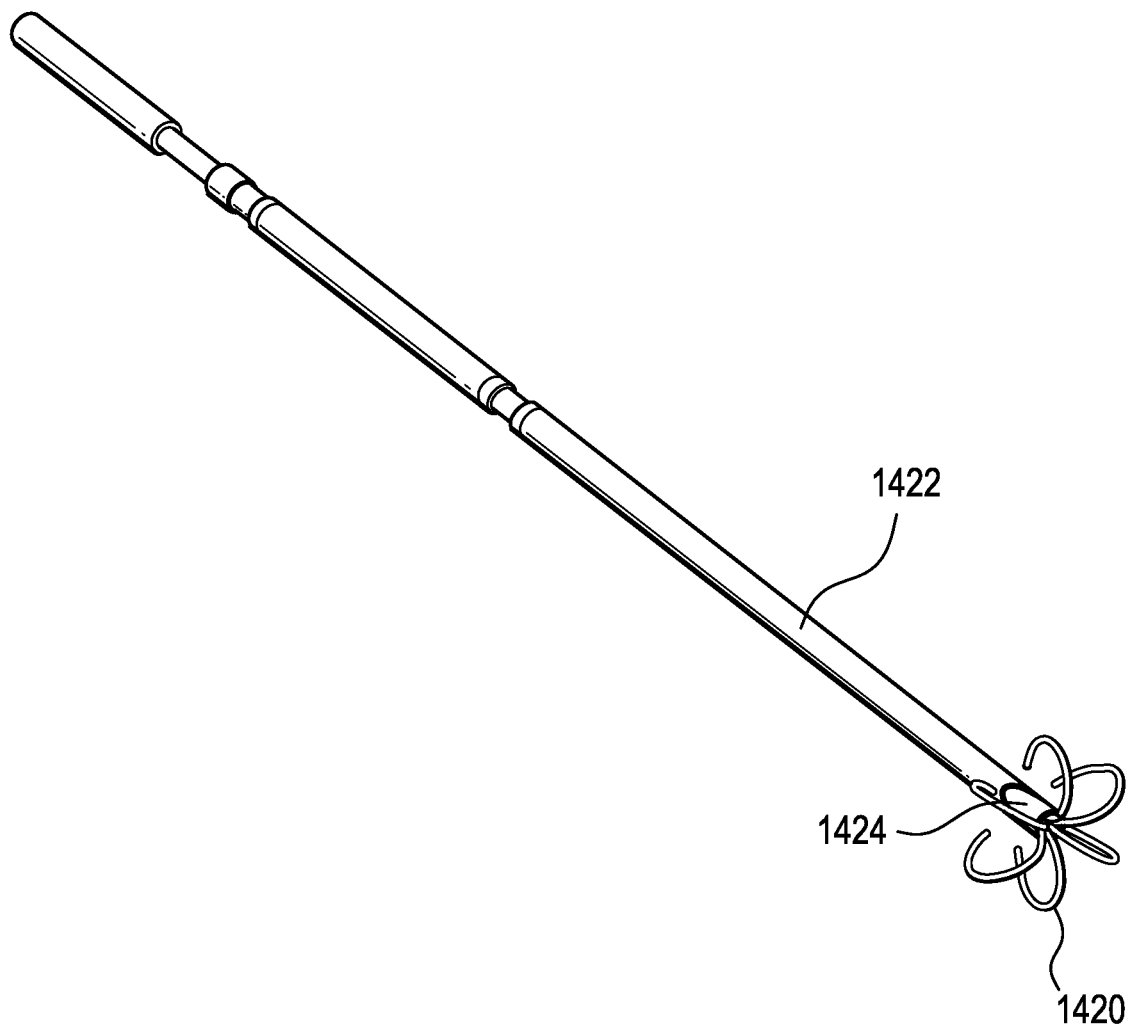
FIG. 5 illustrates an exemplary anchor that may be employed in a lesion removal method in accordance with an embodiment of the invention.

The anchor depicted in FIG. 5 is suitable for use in performing the method for removing tissue lesions described herein. The anchor comprises an outer tube 1422 having a sufficiently sharp edge to pierce the chest cavity tissue and lung without causing excess damage and an inner tube 1424 disposed within outer tube 1422. One or more tines or fingers 1426 formed from shape memory material, e.g., Nitinol, preformed are attached to the end of inner tube 1424. Outer tube 1422 is retractably disposed over inner tube 1424 such that when outer tube 1422 is retracted, tines 1426 assume their preform shape as shown. In keeping with the invention, outer tube 1422 is retracted after it has pierced the lung lesion thereby causing tines 1426 to engage the lung lesion. Other suitable anchors may include coils and suction-based structures.

Figure 6:
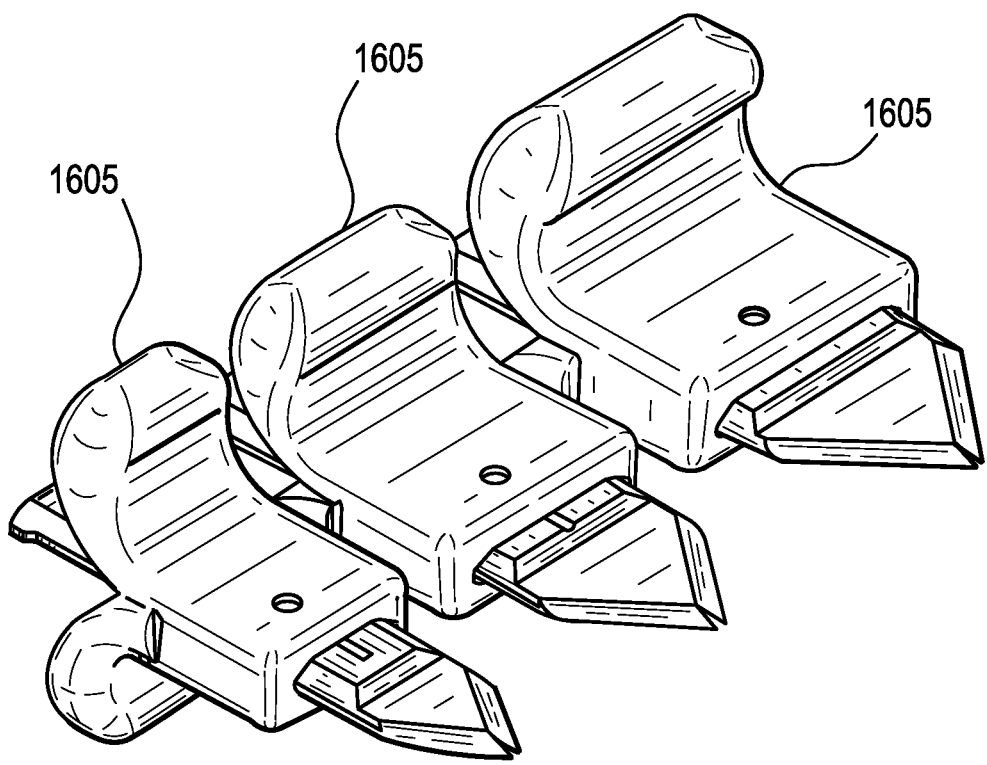
FIG. 6 shows a series of incision blades for use in a lesion removal method in accordance with an embodiment of the invention.

The incision blades depicted in FIG. 6 are suitable for use in performing the method for removing tissue lesions described herein. Once anchor 1400 is set, it is preferable to create a small cut or incision to facilitate insertion of chest wall tissue dilator. Incision blades 1605 are used to make a wider cut. Successive incision blades 1605 include a central aperture which allows them to be coaxially advanced along the anchor needle 1405 to create a wider cut in the chest wall, with each successive blade being larger than the previous blade, thereby increasing the width of the incision.

Figure 7:
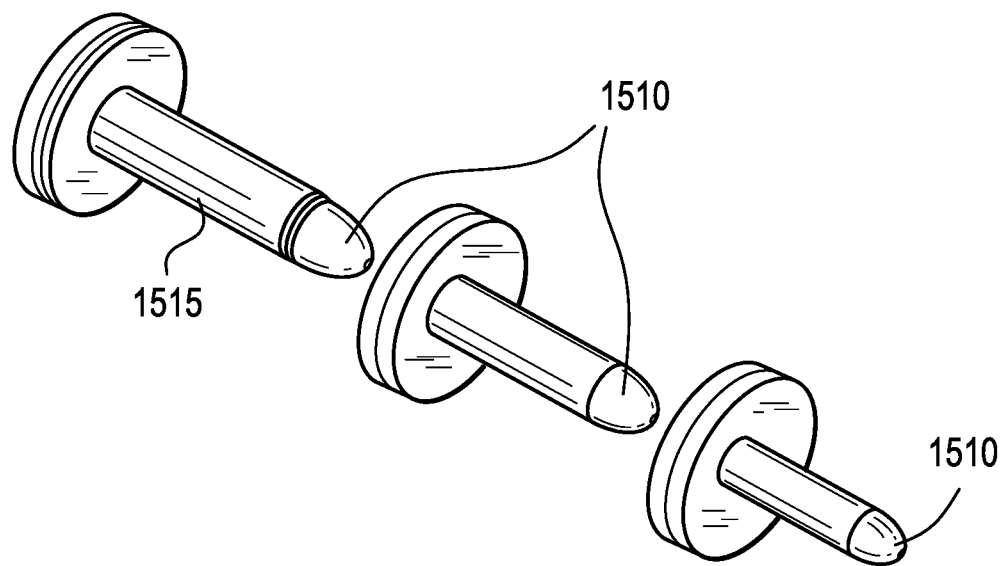
FIG. 7 displays tissue dilators suitable for use in a lesion removal method in accordance with an embodiment of the invention.

The tissue dilator depicted in FIG. 7 is suitable for use in performing the method for removing tissue lesions described herein. The tissue dilator may comprise any suitable device for creating a channel in organic tissue. In one exemplary embodiment, the tissue dilator assembly includes a single cylindrical rod with rounded end 1510 or a cylindrical rod with rounded end and a rigid sleeve arrangement 1515. Successive tissue dilators are coaxially advanced along the anchor needle to create tissue tract or channel in the chest wall, with each successive dilator being larger than the previous dilator, thereby increasing the diameter of the channel. Once the final dilator with rigid sleeve is deployed, the inner rod 1505 is removed while leaving the rigid sleeve in the intercoastal space between ribs to create direct passage to the lung pleura.

Any tissue resection device capable of penetrating lung tissue and creating a tissue core including a target lesion is suitable for use in performing the method for removing tissue lesions described herein. Tissue resection device 1100 described hereinbefore is preferred.

Once tissue resection device 1100 is removed, a small channel in the lung exits where the target lesion was removed. This channel may be utilized to introduce an energy-based ablation device and/or localized chemotherapy depending on the results of the tissue diagnosis. Accordingly, the method and system of the present invention may not only be utilized to ensure an effective biopsy is performed but also complete removal of the lesion with minimal healthy lung tissue removal.

Although shown and described is what is believed to be the most practical and preferred embodiments, it is apparent that departures from specific designs and methods described and shown will suggest themselves to those skilled in the art and may be used without departing from the spirit and scope of the invention. For example, the systems, devices and methods described herein for removal of lesions from the lung. It will be appreciated by the skilled artisan that the devices and methods described herein may are not limited to the lung and could be used for tissue resection and lesion removal in other areas of the body. The present invention is not restricted to the particular constructions described and illustrated, but should be constructed to cohere with all modifications that may fall within the scope of the appended claims.

What is claimed is:

1. A method for removing a tissue lesion comprising blood vessels and airways, the method comprising:
    inserting an anchor through a center portion of the tissue lesion such that a distal end portion of the anchor is positioned at a bottom portion of the tissue lesion;
    creating a channel in tissue leading to the tissue lesion;
    creating a tissue core including the tissue lesion;
    ligating the tissue core at a ligation point downstream from the tissue lesion;
    amputating the tissue core form the tissue between the ligation point and the tissue lesion;
    providing a removal device over the anchor such that the tissue lesion is positioned within an inner diameter of the removal device; and
    removing the tissue core from the channel, the tissue core including sealed vessels and tissue.

2. The method of claim 1, further comprising inserting a sleeve in the channel prior to or after removing the tissue core.

3. The method of claim 2, further comprising anchoring the sleeve to the tissue.

4. The method of claim 2, further comprising delivering localized treatment through the sleeve.

5. The method of claim 1, wherein creating the tissue core includes cauterizing and cutting the tissue.

6. The method of claim 5, wherein ligating the tissue core includes cauterizing the tissue at the ligation point.

7. The method of claim 5, wherein ligating the tissue core includes suturing the tissue at the ligation point.

8. The method of claim 1, wherein amputating the tissue core includes slicing the tissue core.

9. The method of claim 8, wherein amputating the tissue core includes slicing the tissue core with a snare.

10. The method of claim 8, wherein amputating the tissue core includes slicing the tissue core with an energized wire.

11. The method of claim 1, wherein creating the tissue core includes first sealing blood vessels then slicing the tissue to form the tissue core.

* * * * *